Figure 1:
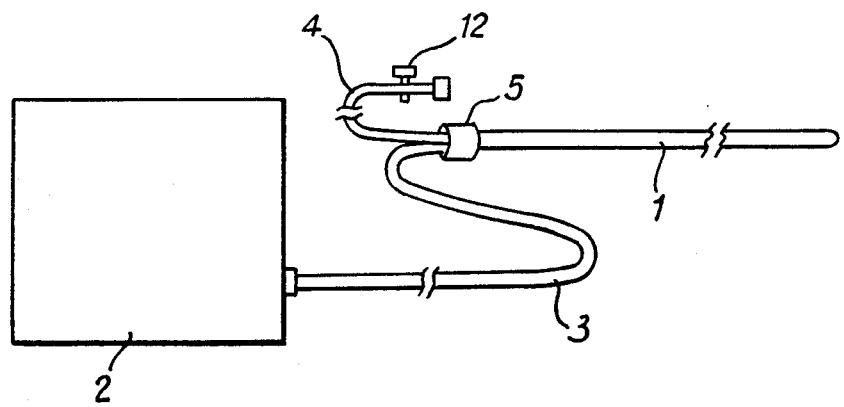

United States Patent [19]

Karcher et al.

[11] Patent Number: 4,856,527

[45] Date of Patent: Aug. 15, 1989

[54] AMNIOSCOPE

[76] Inventors: Gilles Karcher, 2, Rue Lafayette, Nancy, France, 54000; Max Amor, 9, Square de Liege, Vandoeuvre, France, 54500; David Abensour, 27, Rue Hermite; Jean Cinqualbre, 30, Rue Hermite, both of Nancy, France, 54000

[21] Appl. No.: 138,637

[22] Filed: Dec. 28, 1987

[30] Foreign Application Priority Data

Dec. 30, 1986 [FR] France ................... 8618337

[51] Int. Cl.4 ............................ A61B 5/00; A61B 1/06
[52] U.S. Cl. ......................................... 128/634; 128/6; 128/665
[58] Field of Search ...................... 128/4, 6, 632, 633, 128/634, 665, 666, 768; 604/21

[56] References Cited

U.S. PATENT DOCUMENTS

| 3,349,762 | 10/1967 | Kapany | 128/6 X |
| 4,589,404 | 5/1986 | Barath et al. | 128/6 |
| 4,598,715 | 7/1986 | Mächler et al. | 128/634 |

FOREIGN PATENT DOCUMENTS

| 2034870 | 1/1972 | Fed. Rep. of Germany | 128/665 |
| 2215658 | 10/1973 | Fed. Rep. of Germany | 128/665 |
| 2374876 | 8/1978 | France | 128/3 |

Primary Examiner—William H. Grieb
Attorney, Agent, or Firm—Darby & Darby

[57] ABSTRACT

A measuring device 2, containing a light source and a spectrometric analyzer, is connected by an optic fiber cable 3 to a replaceable probe 1 of small diameter, capable of being used even when the cervix uteri is "closed".

15 Claims, 1 Drawing Sheet

AMNIOSCOPE

The invention pertains to an amnioscope, that is, an apparatus for examining the amniotic fluid in utero.

The amniotic fluid, contained in the bag of waters, is normally clear, called "eau de roche", or slightly opalescent. In some pathological circumstances, the fetus may emit meconium, whereby the amniotic fluid loses its bacteriostatic properties and thus entrains a major septic risk for the infant, necessitating prompt delivery.

The procedure of examining the amniotic fluid by means of an amnioscope is known. The classic amnioscopes consist essentially of a transparent rod by which the physician can make an ocular examination of the color of the amniotic fluid. Use of these amnioscopes presents two drawbacks. First of all, the transparent rod has a diameter of about 2 cm, so that its use is limited to the last weeks of the pregnancy, when the neck of the uterus is already partially dilated.

Further, the observation of the color of the amniotic fluid is purely visual and hence subjective, and the risk of error of interpretation is estimated to be about 30%.

It is an object of the present invention to propose an amnioscope that can be used approximately during the last two months of pregnancy, without injury to the cervix uteri.

Another object of the present invention is to propose an amnioscope which permits an objective interpretation of the results, thus reducing the risks of error.

The subject of the invention is an amnioscope with light-conducting probe for examination of the amniotic fluid in utero, characterized in that it comprises: a replaceable probe of small diameter containing optic fibers for the transmission of light to illuminate the amniotic fluid and of light diffused by the amniotic fluid; a measuring device containing a source of light of a defined spectrum and a spectroscopic analyzer; and an optic fiber cable connected on the one hand to said measuring device and, on the other hand, to a connector carrying the probe.

According to other characteristics of the invention:

the probe presents at its distal end a transparent and flexible tip, carried by a tubular sheath;

disposed in the sheath are at least one optical fiber admitting light to the tip and at least one optical fiber transmitting light diffused by the amniotic liquid;

disposed in the sheath is a canal coming out at the distal end of the tip and capable of admitting wash liquid;

the connector carrying the probe is connected by a tube to a source of aseptic liquid;

the probe is covered by a protective envelope, tearable by pulling after the probe has been positioned;

the light source has a spectrum defined to contain the wavelengths of the pigments whose presence is being investigated in the amniotic fluid, and corresponding to meconium, bilirubin, and hemoglobin;

the diameter of the probe is approximately 5 mm, which permits examination of the amniotic fluid even when the cervix uteri is referred to as being "closed".

Figure 2:
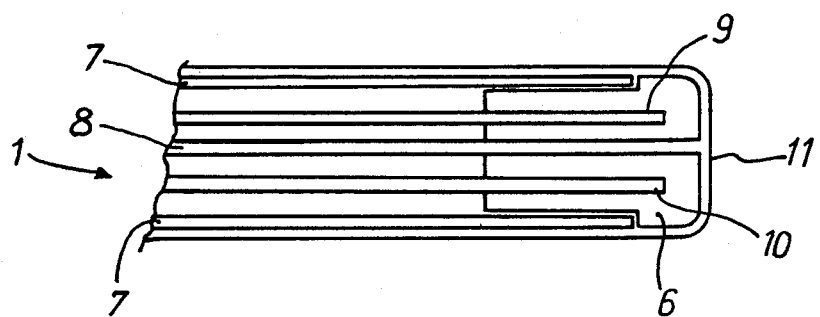

Other characteristics of the invention will be evident from the description which follows, made with reference to the annexed drawing in which one can see:

FIG. 1—an overall diagram of the amnioscope according to the invention;

FIG. 2—a sectional view on a larger scale of the distal end of the probe of the amnioscope.

Referring to FIG. 1, one can see that the amnioscope according to the invention is composed of a probe 1, a measuring device 2, an optic fiber cable 3 connecting the probe and the measuring device, and a tube 4 able to be connected to a source of aseptic liquid. The probe 1 has a diameter of about 5 mm and a length of about 30 cm. Its proximal end has a connector 5 ensuring connection to the cable 3 and to the tube 4.

The probe 1 (FIG. 2) has a distal end consisting of a transparent, flexible tip 6 of a form adapted not to be traumatizing to the bag of waters. This tip 6 is carried by a tubular sheath 7. At, for example, the middle of tip 6 there emerges a canal 8 able to feed a liquid for washing the distal end of the probe.

In the connector 5, the canal 8 is connected to the tube 4. Near the end of tip 6, and in the body of the tip, optic fibers end—at least one light-admitting fiber 9 and at least one observation fiber 10. These fibers are lodged in the sheath 7, as is the canal 8 for admission of the wash liquid, and they are optically connected to the cable 3 through the connector 5.

Around probe 1 is provided, preferably, a protective envelope 11, easily tearable by simple pulling at its part near the connector 5. This envelope 11 is intended to be withdrawn after the probe has been put in place. Its role is to protect, during positioning, the distal end of the probe from any trace of a product that could affect either the optical transmission or the result of the observation.

By reason of its small diameter, about 5 mm, the probe can be used even when the cervix uteri is referred to as being "closed", that is, from the eighth month of pregnancy on. Probe 1 being in place, the tearable envelope 11 is removed. By means of a cock 12 (FIG. 1) the distal end of the probe can be washed using a suitable liquid passing through canal 8. Obviously it is possible to use only one of the means for protection of the end of the probe—the tearable outer envelope 11 or washing with a liquid admitted through canal 8.

The measuring device 2 comprises a source of light of defined spectrum, a spectroscopic analyzer, a display and controls. As all these elements are known in themselves, they are not described. Through the optic fiber 9 the light source transmits a light of defined spectrum, to the level of the bag of waters.

Through the fiber 10, the spectrometric analyzer receives the light diffused by the amniotic fluid, and it analyzes it qualitatively to determine the presence, in the amniotic fluid, of the colorations characteristic of certain substances revealing an anomaly or a pathological state of the fetus.

Green coloration is linked with the presence of meconium, yellow coloration with the presence of bilirubin, and red coloration with the presence of hemoglobin.

The spectrometric analyzer automatically performs a qualitative spectrometric analysis adapted to the colorations to be recognized, that is, to the characteristic pigments corresponding to these colorations. This analysis is carried out in the classic manner by a combination of color filters and light detectors.

The analysis is not necessarily quantitative, so that a simplified spectrometric analyzer may be used for the recognition of certain pigments characterized by specific wavelengths. Because of this specificity, the spectrometric analyzer gives an objective and sure result, more reliable than a purely visual examination. The spectrum of the light emitted by the source is defined to contain the wavelengths characteristic of the pigments investigated.

According to the present invention, probe 1 is replaceable. It can be reusable after sterilization, or simply dispensable because of its low cost.

In the description of FIG. 2 there was mentioned a light-admitting optic fiber 9 and an optic fiber 10 for observation. It goes without saying that the admission of light to the distal end of the probe can be ensured by several fibers 9, just as the transmission of the light diffused by the amniotic fluid can be ensured by several fibers 10.

As compared with the existing instruments, the amnioscope according to the invention presents two important advantages:

owing to the small diameter of the probe, it can be used even when the cervix uteri is "closed", that is, from the eighth month of pregnancy on;

owing to the objectivity of the test done with the spectrometric analyzer, the diagnosis is more reliable.

We claim:

1. An amnioscope for examining an amniotic fluid in utero, comprising:
    light transmission means for transmitting light of a defined spectrum to illuminate the amniotic fluid and for transmitting the light after being diffused by the amniotic fluid, said light transmission means being flexible so as to not traumatize a bag of waters containing the amniotic fluid;
    means for recognizing pigments in the amniotic fluid, said recognizing means including means for illuminating the amniotic fluid with the light of the defined spectrum and means for spectroscopically analyzing the light after being diffused by the amniotic fluid; and
    means for conveying the light of the defined spectrum between said illuminating means and said light transmission means and for conveying the light after being diffused by the amniotic fluid between said light transmission means and said spectroscopically analyzing means.

2. An amnioscope according to claim 1, characterized in that the transparent and flexible tip is carried by a tubular sheath.

3. An amnioscope according to claim 2, characterized in that there are disposed in the sheath at least one optic fiber for admission of light to the tip and at least one optic fiber for transmission of the light diffused by the amniotic fluid.

4. An amnioscope according to claim 2, characterized in that in the sheath a canal is disposed leading out at the distal end of the tip (6) and able to admit the wash liquid.

5. An amnioscope according to claim 1, characterized in that the connector carrying the probe is connected by a tube to a source of aseptic liquid.

6. An amnioscope according to claim 1, characterized in that the probe is covered by a protective envelope tearable by pulling after the probe has been positioned.

7. An amnioscope according to claim 1, characterized in that the light source has a spectrum defined to contain the wavelengths of the pigments whose presence is being investigated in the amniotic fluid, and corresponding to meconium, bilirubin, and hemoglobin.

8. An amnioscope according to claim 1, characterized in that the diameter of the probe (9) is about 5 mm, so as to permit the examination of the amniotic fluid even when the cervix uteri is "closed".

9. An amnioscope according to claim 1, further comprising:
    a light conducting probe with a distal end, said light transmission means being transparent and being at said distal end so as to constitute a transparent and flexible tip.

10. An amnioscope according to claim 1, wherein said illuminating means includes a light source.

11. An amnioscope according to claim 1, wherein said conveying means includes optical fibers.

12. A method for examining an amniotic fluid in utero, comprising the steps of:
    illuminating an amniotic fluid with light of a defined spectrum, the step of illuminating including conveying the light to a light transmissible element and transmitting the light through the light transmissible element to illuminate the amniotic fluid, the light transmissible element being flexible so as to not traumatize a bag of waters containing the amniotic fluid;
    conveying the light after being diffused by the amniotic fluid from the light transmissible element; and
    recognizing pigments in the amniotic fluid by spectroscopically analyzing the conveyed light that was diffused by the amniotic fluid.

13. A method according to claim 12, further comprising carrying the light transmissible element by a sheath, and admitting wash fluid into a canal in the sheath.

14. A method according to claim 12, further comprising:
    protecting the light transmissible element with a protective envelope; and
    pulling the envelope away so as to tear the envelope after the light transmissible element is in position relative to the bag of waters to effect the step of recognizing.

15. A method according to claim 12, wherein the step of recognizing is effected when a cervic uteri is closed.

* * * * *